United States Patent [19]

Geria et al.

[11] Patent Number: 4,780,309

[45] Date of Patent: Oct. 25, 1988

[54] EDIBLE AEROSOL FOAM COMPOSITIONS AND METHOD OF PREPARING SAME

[75] Inventors: Navin M. Geria, Warren; Shirley A. Barcelon; Alfred Oppenheimer, both of Randolph; Mamoun M. Hussein, Mountain Lakes, all of N.J.

[73] Assignee: Warner-Lambert Company, Morris Plains, N.J.

[21] Appl. No.: 62,936

[22] Filed: Jun. 16, 1987

[51] Int. Cl.$^4$ ................................................ A61L 9/04
[52] U.S. Cl. ...................................... 424/45; 514/945
[58] Field of Search ........................... 424/45; 514/945

[56] References Cited

U.S. PATENT DOCUMENTS

| | | | |
|---|---|---|---|
| 3,419,658 | 12/1968 | Sanders | 424/45 |
| 3,490,923 | 1/1970 | Eiseman, Jr. | 424/45 |
| 4,639,367 | 1/1987 | Mackles | 424/45 |

OTHER PUBLICATIONS

"CAB-O-SIL" Cabot Corporation, 1969 pp. 1 to 10, and 63.

Primary Examiner—John E. Kittle
Assistant Examiner—P. J. Ryan
Attorney, Agent, or Firm—Charles A. Gaglia, Jr.

[57] ABSTRACT

A procedure for preparing a palatable aerosol foam of unpleasant edible oil containing up to 80% oil is disclosed. This has been achieved by incorporating an inorganic complexing agent, water, a sweetening agent, a sensory masking agent and a propellant present in an amount sufficient by itself to function as the whipping agent and propellant into the oil to form a pleasant tasting suspension without an oily mouthfeel, unpalatable taste and unpleasant odor. Each teaspoon of aerosol foam will contain from about 2 to 4 grams of oil.

28 Claims, No Drawings

EDIBLE AEROSOL FOAM COMPOSITIONS AND METHOD OF PREPARING SAME

The present invention relates to aerosol foam compositions of unpleasant edible oils which render the unpleasant edible oils essentially free of unpleasant odor, taste and mouthfeel and a method of preparation.

BACKGROUND OF THE INVENTION

The use of edible oils for medicinal and nutritional purposes is well known. For example, cod liver oil is used as a nutritional supplement of vitamins A and D. Castor oil and mineral oil are used as cathartics. Marine oils and marine oil concentrates containing omega-3 fatty acids are recommended for the prevention of coronary heart disease, migraine headaches, arthritis and some allergies. Edible oils are useful as vehicles for the delivery of medicaments both topically and internally. Many edible oils are equally well known for their unpalatable taste, unpleasant odor and unpleasant mouthfeel.

The edible oils utilized in the present invention are varied and may be of animal, vegetable and mineral origin. These oils are well known ingredients in edible products such as foods and pharmaceuticals. Such oils are generally distasteful and difficult to swallow when taken orally. Oils are difficult for most people to ingest because they are greasy, oily somewhat viscous fluids. In addition, many edible oils have an unpalatable taste and unpleasant odor. Typical among the unpleasant edible oils useful for the present invention are marine oils such as fish liver oil, fish oil, whale oil, seal oil, marine oil concentrates, and marine oils containing omega-3 fatty acids; and vegetable oils such as castor oil, linseed oil and the like.

The process of obtaining marine oils, that is oil-expression, leads to the formation of amines which are in combination with the marine oil. In addition, marine oil contains highly unsaturated fatty acids which are oxidized during storage forming aldehydes and alcohols. The amines and oxidation products result in an unpleasant odor and taste. Oils that initially had no perceptible odor or off taste will develop an unpleasant, odor and/or taste with time.

Oils particularly useful in the present invention are fresh marine oils rich in all-cis-5,8,11,14,17-eicosapentaenoic acid (EPA) and all-cis-4,7,10,13,16,19 docosahexaenoic acid (DHA). These acids, commonly referred to as omega-3 fatty acids, are known to reduce platelet aggregation, thrombotic tendencies and blood viscosity in normal adults. In addition, omega-3 fatty acids have been found to reduce elevated serum cholesterol, triglycerides, cholesterol rich low density lipoproteins and triglyceride rich very low density lipoproteins in adults with elevated serum cholesterol.

Capsules, tablets and liquids are the most common dosage forms for the oral administration of unpleasant edible oils. Many people have difficulty swallowing capsules and tablets. This problem is exacerbated by the larger size tablets and capsules often required in oil based products.

U.S. Pat. No. Re. 18,719 discloses a process for making cod liver oil tablets. The cod liver oil extractives are applied to charcoal in the presence of a volatile solvent and other ingredients. Volatile solvent is removed and the particles made into tablets. Oil content is 7 to 30% of the tablet weight.

U.S. Pat. No. 1,845,370 discloses a stable cod liver oil and water emulsion stabilized with a calcium phosphorous compound and acacia with sugar added to sweeten the composition.

U.S. Pat. No. 1,638,700 discloses a powdered fish oil product which is designed for use as a stock conditioner or vitamin supplying agent or enricher for animal foods. Oil is combined with a mineral carrier such as the non-metallic minerals especially calcium and magnesium groups, as for example, calcium carbonate, calcium palmitrate, calcium lactate, calcium glycolate, calcium saccharate, calcium hydrate, calcium oxide, calcium stearate, or other similar calcium salts or calcium minerals. Minerals of the magnesium group which may be used are magnesium carbonate, magnesium oxide, magnesium silicate, and other magnesium salts or magnesium compounds.

Final fish oil content of the product may be up to 60 percent (60%).

South African Pat. No. 63/809 discloses an aqueous multiple vitamin composition having an oil phase dispersed therein to form an emulsion. The oral phase can be any non-toxic orally acceptable animal or vegetable oil.

Japanese Pat. No. J56169-622 discloses preparing a solid drug containing an oily liquid effective ingredient by absorbing the oil liquid and a nonionic surfactant on a granular powder such as aluminum magnesium hydroxide, magnesium metasilicate aluminate, magnesium oxide and aluminum hydroxide.

U.S. Pat. No. 4,623,489 discloses deodorizing edible oils by refining the oils by deaerating the oil during the degumming steps and the acid-$H_2O$ washing.

U.S. Pat. No. 4,623,488 discloses refined fish oil produced by (a) preliminary molecular distillation of a mixture of polyhydric alcohol, a monoglyceride and a fish oil to remove volatile components and deodorize fish oil.

U.S. Pat. No. 4,639,367 discloses a foamable, edible oil anhydrous aerosol foam delivery system for solid particulate therapeutic agents. The aerosol foam composition comprises a foamable liquid oil, a foaming agent, a propellant and dispersed solid particles, said particles comprising an active therapeutic agent.

Tablets and capsules solve the unpleasant taste and odor of the oils by avoiding oral contact. The oil being entrapped within the tablet or capsule is physically not available for smell or taste. The limitation of these dosage forms is that they can deliver only small amounts of the oil per dose. The recommended adult dose for castor oil is 5 ml two to four times a day. While the therapeutic dose for marine oil and marine oil concentrates is about 12 to 15 grams per day. Since a large pharmaceutical capsule contains about 1 gram of oil, equal to about 1 ml, the use of capsules would be both inconvenient and expensive. Tablets are capable of delivering even less oil than capsules. A one gram tablet would contain only about 25 to 30 percent oil. In addition, many people have difficulty in swallowing capsules and tablets.

Animal, vegetable and mineral oils produce an oily unpleasant mouthfeel when placed in the mouth. In addition, the unpleasant edible oils of the present invention have, in the case of marine oils, a distinct fishy odor and taste, while vegetable oils such as castor and linseed have an acrid taste and a decidedly nauseating aftertaste. Also, the low density of oils often contributes to esophageal reflux. This condition occurs as the oils, floating on the upper surface of the stomach contents, reenter the lower end of the esophagus resulting in a retasting sometimes nauseating effect.

It is desirable therefore to deliver large doses of unpleasant edible oils without the unpleasant odor, taste and mouthfeel problems associated with these oils.

SUMMARY OF THE INVENTION

A procedure for preparing a palatable aerosol foam of unpleasant edible oil which may contain up to 80% by weight oil and deliver 2 to 4 grams of oil per teaspoon has been unexpectedly discovered. This has been achieved by incorporating an inorganic complexing agent, water, propellant, a sweetening agent and a sensory masking agent into the oil to form a pleasant tasting aerosol foam without an oily mouthfeel, unpalatable taste and unpleasant odor. The inorganic complexing agent forms a viscosity increasing complex with the oil and the flavor composition masks the taste and odor of the oil.

DETAILED DESCRIPTION

In particular, it has been found that a palatable, aerosol foam of unpleasant edible oil is produced from an admixture of about 80% to about 20% by weight of an unpleasant edible oil, an inorganic complexing agent in an amount from about 4% to about 30% by weight, about 0.5% to about 8% by weight of a sensory masking agent, about 5% to about 30% by weight water, about 5% to about 50% propellant by weight and a sweetening agent in an amount of about 0.02% to about 10% by weight. All weights are in percent of the total composition.

While the invention is not to be limited to theoretical considerations, it is believed that the palatable mouthfeel and taste of the present invention is the result of several factors. It is believed that the oily mouthfeel is overcome by the complex formed between the inorganic complexing agent and the oil. This complex acts to increase oil viscosity allowing the sweetening agent to be uniformly suspended. The complex appears to modify the surface tension of oil allowing it to pass through the oral cavity with less of a coating effect and therefore a less oily mouthfeel. The oil complex, which is stable in water, is more dense than oil alone and more dense than water. The dense oil complex does not float on the surface of the stomach contents and therefore reduces or eliminates esophageal reflux and its undesirable effects.

It is further believed that the sensory masking agent masks the odor and taste of the oils. The taste masking may occur as the flavoring agent selectively blocks or saturates sensory sites in the mouth and nose. It is believed that a combination of the effects recited above prevent the unpleasant taste, odor and mouthfeel generally associated with unpleasant edible oils.

The oils useful in the present invention are varied and may be of animal, vegetable and mineral origin. Methods of producing oils are known and not a subject of the present invention. Animal oils are derived from the organs and tissues of animals and may be collected through extraction, heating and/or expressing processes. Vegetable oils are usually derived from the seeds of various plants and are generally produced by extraction or a pressing process. Throughout the specification and claims, the term oil shall be defined as any oil of animal or vegetable origin in liquid form at the time of addition of the inorganic complexing agent.

Illustrative, non-limiting examples of oils useful in the present invention include animal oils such as the marine oils: fish oil, whale oil, fish liver oil, seal oil, oils containing at least one omega-3 fatty acid and the like; vegetable oils such as castor oil, linseed oil, oils containing at least one omega-3 fatty acid and the like; mineral oil and the like and mixtures thereof. In a preferred embodiment, the marine oil comprises from about 10% to about 60% of at least one omega-3 fatty acid.

The unpleasant oil is present in an amount of about 20% to about 80%, preferably about 40% to about 80%, and most preferably about 40% to about 70% by weight of the total aerosol foam composition.

The complexing agent is characterized by being insoluble in oil, being inorganic and by forming a complex with the oil such that the viscosity of the oil is increased.

The inorganic complexing agents are incorporated into the oil in particulate form. The particle size may vary widely depending on the particular complexing agent but must be of adequate size to enable incorporation into the oil without exhibiting a gritty or sandy feel. In addition, the particle size must be adequate to enable complex formation with the oil. Exemplary particle size ranges may be from about 0.1 micrometers to about 300 micrometers, preferably about 0.5 micrometers to about 150 micrometers and most preferably about 0.5 micrometers to about 100 micrometers.

The inorganic complexing agent may be selected from a wide range of compounds that are insoluble in oil and provide complexation of oil when admixed with oil. Exemplary inorganic complexing agents may be selected from the group consisting of magnesium trisilicate, calcium carbonate, calcium silicate, a co-dried gel of aluminum hydroxide and magnesium carbonate, magnesium carbonate, ground limestone, ground oyster shells, and mixtures thereof.

The change in oil viscosity with increasing complexing agent concentration is a continuum. Free flowing liquids are formed at low complexing agent concentrations and thick, essentially nonflowing compositions having a texture like that of petroleum jelly are formed at the higher complexing agent concentrations.

The ratio of inorganic complexing agent to oil will determine the viscosity or degree of thickening of the oil. A complexing agent to oil ratio of about 1:99 to about 1:10 will produce liquids having a gradual increase in viscosity. Complexing agent to oil ratios of about 1:9 to about 1:3 will produce liquids with the consistency of syrups. Complexing agent to oil ratios of about 1:2.5 to about 1:1 will produce semisolids having the consistency of creams to ointments. Complexing agent to oil ratios greater than about 1:1 will produce solids. The texture of the solids will become granular and change to a powder as the complexing agent to oil ratio increases beyond about 1.2:1. In general, complexing agent to oil ratios of about 1:5 to about 1:3 will produce compositions useful in the present invention.

The inorganic complexing agent is present in an amount of about 4% to about 30%, preferably about 10% to about 30% and most preferably about 10% to about 20% by weight of the total suspension composition.

The interaction of oil and inorganic complexing agent useful in the present invention is described in detail in copending application field on even date herewith, Ser. No. 62,927, entitled "Oil Compositions of Increased Viscosity and Method of Preparing Same,"

the entire contents of which are hereby incorporated by reference.

Water is included in the present invention in amounts of about 3% to about 30% preferably about 5% to about 25% and most preferably about 5% to about 10% by weight of the total composition. A water content of less than about 3% will not produce a foam. A water content of 30% will still form a good foam but will deliver lower amounts of oil thus defeating one of the advantages of the present invention that is the ability to deliver an aerosol foam with a high oil content.

The propellant of the present invention must be an edible material that is gaseous under atmospheric pressures and liquified when compressed. The most commonly used are propane, butane, isobutane and mixtures thereof. The fluorocarbons such as "Freon 115" and the like are also useful. In addition, compressed gases such as nitrogen and carbon dioxide are also useful. Propane, propane-butane and propane-isobutane mixtures are preferred propellants.

The amount of propellant used in the present invention is from about 5% to about 50%, preferably about 10% to about 40% and most preferably about 15% to about 25%. Propellant content of less than 5% does not produce a foam. Propellant content of greater than 50% increases the cost of the aerosol while decreasing the amount of oil in the foam.

The sweetening agent may be selected from solid natural or synthetic sweeteners capable of imparting high intensity sweetness. These sweeteners are selected from the group consisting of amino acid based sweeteners, dipeptide sweeteners, glycyrrhizin, aspartame, saccharin and its salts, acesulfame and its salts, cyclamate and its salts, steviosides, talin, dihydrochalcone compounds sucralose and mixtures thereof.

The sweeteners may be used in amounts necessary to impart sweetness and preferably in amounts of about 0.02 to about 10% by weight of the composition. Aspartame, saccharin and its salts are the preferred sweeteners and may be used in amounts of about 0.2% to about 5% and about 0.2% to 2.5% respectively, by weight of the composition. The preferred amounts of these sweeteners are about 0.3% to about 2%, most preferably about 0.5% to about 1.5%.

Sensory masking agents useful in the present invention are described in detail in the copending application filed on even date herewith, Ser. No. 62,930, entitled "Taste and Odor Masked Edible Oil Compositions", the entire contents of which are hereby incorporated by reference. The term "sensory masking agent" is defined as relating to an agent that masks unpleasant taste, unpleasant odor or both unpleasant taste and unpleasant odor of an oil.

The sensory masking agent is present in an amount sufficient to sensory mask the unpleasant edible oil resulting in a pleasant edible oil. In general, the sensory masking agent is present in an amount of from about 0.5% to about 8%, preferably from about 1% to about 8%, and most preferably from about 3% to about 6% by weight of the total composition.

Sensory masking agents useful in the present invention are varied and may mask odor, taste or odor and taste.

Illustrative non-limiting examples of sensory masking agents useful in masking taste and odor or unpleasant oils in the present invention include taste and odor masking agents such as anethole, dihydroanethol, eugenol, wintergreen and the like; taste masking agents such as vanillin, ethyl vanillin, ethyl maltol and the like; and odor masking agents such as natural and artificial; lime, lemon, orange, pineapple, grapefruit, cinnamon, clove, bay, allspice, anise, spearmint, peppermint, benzaldehyde, cherry, and the like and mixtures thereof. Any of the masking agents may be used individually or in mixtures.

It is believed that odor masking agents useful in the present invention are volatile compositions having at least one component with a boiling point less than about 250° C. and greater than about 150° C. Odor masking agents having boiling points greater than about 250° C. do not volatilize from the edible oil in sufficient quantity to mask odor. Odor masking agents having boiling points less than about 150° C. would volatize too rapidly to provide a sustained odor masking.

Sensory masking agents such as the flavor oils do not have sufficient water solubility to mask taste from the oil compositions of the present invention.

In preferred embodiments of the present invention, combinations of taste masking and odor masking agents are utilized to produce very pleasant taste and odor masked compositions. Combinations of a taste masking agent such as vanillin and an odor masking agent such as a natural and artificial fruit or mint oil produce especially pleasant tasting and pleasant smelling compositions.

There may also be incorporated in the aerosol foam of the present invention additional nonessential ingredients such as colorants, humectants, texturizing agents preservatives, colorants and the like.

Texturizing agents are useful in the present invention to further improve mouthfeel and reduce the oil sensation generally associated with ingesting oily compositions. Suitable texturizing agents are particulate materials, insoluble in oil, that act as an osmotic agent taking up moisture in preference to oil. The particle size must be adequate to enable incorporation into the oil without exhibiting a gritty or sandy mouthfeel.

Texturizing agents are preferably without sweetness, however, crystalline sweetening agents such as sucrose, dextrose, fructose, corn syrup solids, and the sugar alcohols such as; sorbitol, mannitol, xylitol and the like may be used. In addition, nonsweetening agents such as maltodextrin, polydextrose, various dextrins and the like may be used. A particularly preferred texturizing agent is maltodextrin.

The texturizing agent is present in amounts up to about 20%, preferably from about 1% to about 20% and most preferably from about 2% to about 10% by weight of the total composition.

Preservatives such as benzoic acid, sorbic acid, methylparaben, propylparaben, dl-alpha tocopherol, BHT, and ethylene-diaminetetracetic acid (EDTA). Preservatives are generally present in amounts up to about 1% and preferably from about 0.01% to about 0.5% by weight of the composition.

Colorants useful in the present invention, include the pigments which may be incorporated in amounts of up to about 2% by weight of the composition. A preferred pigment, titanium dioxide, may be incorporated in amounts of up to about 1% by weight. Also, the colorants may include other dyes suitable for food, drug and cosmetic applications, and known as F.D. & C. dyes and the like. The materials acceptable for the foregoing spectrum of use are preferably oil soluble. A full recitation of all F.D. & C. and D. & C. colorants and their corresponding chemical structures may be found in the Kirk-Othmer Encyclopedia of Chemical Technology, 3rd edition, in Volume 6, at pages 561-595, which text is accordingly incorporated herein by reference.

Compositions of the present invention are prepared by admixing the oil and complexing agent until a homogeneous mixture of increased viscosity is obtained. The sensory masking agent, water and sweetener are added with continued mixing until a uniform mixture is formed. Additional ingredients such as colorants, preservatives and texturizing agents may be added with continued mixing until a uniform mixture is formed. Charging the resulting composition to an aerosol container and charging the container with a food grade propellant in an amount sufficient by itself to function as the whipping agent and propellant. The order of addition of ingredients to the complexed oil is not critical and may be varied.

Preferably, the compositions of the present invention are prepared at room temperature. When required, however, the compositions may be prepared at elevated or reduced temperatures.

The admixing of oil and inorganic complexing agent may be at low shear or high shear. Low shear mixing is preferred as it is less likely to cause degradation of oil components. The mixture of oil and inorganic complexing agent may be at a temperature just above the freezing point of the oil up to just below the decomposition temperature of the oil. In general mixing of the oil and inorganic complexing agent occurs at about 15° C. to about 70° C., preferably from about 15° C. to about 50° C. and most preferably from about 15° C. to about 30° C.

The mixing of the oil and inorganic complexing agent may be performed under an inert atmosphere such as nitrogen or carbon dioxide. The preparation of compositions containing oxidizable materials such as omega-3 acids is preferably conducted in an inert atmosphere.

The present invention is further illustrated by the following examples. All parts and percentages in the examples and throughout the specification and claims are by total weight of the compostion unless otherwise indicated.

EXAMPLE 1

(Inventive Run 1)

This example demonstrates a method for preparing a palatable aerosol foam of castor oil. The ingredients are mixed in the order indicated.

| No. | Ingredient | Percent (w/w) |
| --- | --- | --- |
| 1. | Castor Oil | 53.85 |
| 2. | Magnesium trisilicate | 15.00 |
| 3. | Water | 7.70 |
| 4. | Maltodextrin | 3.80 |
| 5. | dl-alpha tocopherol | 0.02 |
| 6. | Flavor (w/w) | 3.50 |
|  | Lemon oil    5 × 80% |  |
|  | Vanillin           5% |  |
|  | Alcohol          15% |  |
| 7. | Aspartame (sweetener) | 0.73 |
| 8. | Propellant | 15.40 |

Procedure

The oil and magnesium trisilicate are mixed until a homogeneous mixture of increased viscosity is obtained. The water, maltodextrin, dl-alpha tocopherol, flavor and aspartame are added with continued mixing until a homogeneous suspension is formed. Charging the resulting composition to an aerosol container and charging the container with a food grade propellant in an amount sufficient by itself to function as the whipping agent and propellant.

The final composition will produce a foam, have a palatable mouthfeel, a pleasant taste and a pleasant odor.

EXAMPLE 2

(Inventive Run 2)

This example demonstrates a method for preparing a palatable aerosol foam of fish oil. The ingredients are mixed in the order indicated.

| No. | Ingredient | Percent (w/w) |
| --- | --- | --- |
| 1. | Fish Oil | 53.85 |
| 2. | Magnesium trisilicate | 15.00 |
| 3. | Water | 7.70 |
| 4. | Maltodextrin | 3.80 |
| 5. | dl-alpha tocopherol | 0.02 |
| 6. | Flavor (w/w) | 3.50 |
|  | Lemon oil    5 × 80% |  |
|  | Vanillin           5% |  |
|  | Alcohol          15% |  |
| 7. | Aspartame (sweetener) | 0.73 |
| 8. | Propellant | 15.40 |

Procedure

The oil and magnesium trisilicate are mixed until a homogeneous mixture of increased viscosity is obtained. The water, maltodextrin, dl-alpha tocopherol, flavor and aspartame are added with continued mixing until a homogeneous suspension is formed. Charging the resulting composition to an aerosol container and charging the container with a food grade propellant in an amount sufficient by itself to function as the whipping agent and propellant.

The final composition produces a foam, has a palatable mouthfeel, a pleasant taste and a pleasant odor.

EXAMPLE 3

(Inventive Run 3)

This example demonstrates a method for preparing a palatable aerosol foam of cod liver oil. The ingredients are mixed in the order indicated.

| No. | Ingredient | Percent (w/w) |
| --- | --- | --- |
| 1. | Cod Liver Oil | 53.85 |
| 2. | Magnesium trisilicate | 15.00 |
| 3. | Water | 7.70 |
| 4. | Maltodextrin | 3.80 |
| 5. | dl-alpha tocopherol | 0.02 |
| 6. | Flavor (w/w) | 3.50 |
|  | Lemon oil    5 × 80% |  |
|  | Vanillin           5% |  |
|  | Alcohol          15% |  |
| 7. | Aspartame (sweetener) | 0.73 |
| 8. | Propellant | 15.40 |

Procedure

The oil and magnesium trisilicate are mixed until a homogeneous mixture of increased viscosity is obtained. The water, maltodextrin, dl-alpha tocopherol, flavor and aspartame are added with continued mixing until a homogeneous suspension is formed. Charging the resulting composition to an aerosol container and charging the container with a food grade propellant in an amount sufficient by itself to function as the whipping agent and propellant.

The final composition will produce a foam, have a palatable mouthfeel, a pleasant taste and a pleasant odor.

This invention being thus described, it will be obvious that the same may be varied in many ways. Such variations are not to be regarded as a departure from the spirit and scope of the invention and all such modifications are intended to be included within the scope of the following claims.

We claim:

1. A palatable aerosol foam composition of unpleasant edible oil comprising:
   about 20% to about 80% of an unpleasant edible oil;
   about 4% to about 30% of an inorganic complexing agent insoluble in oil;
   about 3% to about 30% of water;
   a sensory agent present in an amount sufficient to sensory mask the unpleasant edible oil resulting in a pleasant edible oil;
   a sweetening agent; and
   an edible propellant in an amount of about 5% to about 50%;
   wherein said inorganic complexing agent is selected from the group consisting of magnesium trisilicate, calcium carbonate, calcium silicate, a codried gel of aluminum hydroxide and magnesium carbonate, magnesium carbonate, ground limestone, ground oyster shells and mixtures thereof forms a viscosity increasing complex with the oil and the sensory masking agent masks the taste and odor of the oil and the propellant is present in an amount sufficient by itself to function as the whipping agent and propellant.

2. The composition of claim 1 wherein the sensory masking agent is present in an amount of about 0.5% to about 8% by weight of the total composition.

3. The composition of claim 1 wherein the unpleasant edible oil is selected from the group consisting of vegetable oil, marine oil, mineral oil and mixtures thereof.

4. The composition of claim 1 wherein the vegetable oil is selected from the group consisting of caster oil, linseed oil and mixtures thereof.

5. The composition of claim 1 wherein the oil is a marine oil is selected from the group consisting of fish liver oil, fish oil, whale oil, seal oil, marine oil concentrates, marine oils containing at least one omega-3 fatty acid and mixtures thereof.

6. The composition of claim 1 wherein the oil is fish oil.

7. The composition of claim 1 wherein the oil is marine oil and the marine oil comprises from about 10% to about 60% of at least one omega-3 fatty acid by weight of the fish oil.

8. The composition of claim 1 wherein the sweetening agent is present in an amount from about 0.02% to about 10% by weight of the total composition.

9. The composition of claim 1 wherein the complexing agent is magnesium trisilicate.

10. The composition of claim 1 wherein the sweetener is selected from the group consisting of amino acid based sweeteners, dipeptide sweeteners, aspartame, glycyrrhizin, saccharin and its salts, acesulfame and its salts, cyclamate and its salts, steviosides, talin, dihydrochalcone compounds, sucralose and mixtures thereof.

11. The composition of claim 1 wherein the sensory masking agent is selected from the group consisting of a taste masking agent, an odor masking agent and mixtures thereof.

12. The composition of claim 1 wherein the taste masking agent is selected from the group consisting of: anethole, dihydroanethole, eugenol, vanillin, ethyl vanillin, ethyl maltol and mixtures thereof, and the odor masking agent is selected from the group consisting of natural and artificial; lime, lemon, orange, pineapple, grapefruit, cinnamon, clove, bay, allspice, anise, wintergreen, spearmint, peppermint, benzaldehyde, cherry and mixtures thereof.

13. The composition of claim 1 further comprising a texturizing agent in an amount up to about 20% by weight of the composition.

14. The composition of claim 1 further comprising a preservative in an amount of about 0.0% to about 1% by weight of the composition.

15. A process for preparing a palatable aerosol foam composition of unpleasant edible oil which comprises:
    admixing about 20% to about 80% of the edible oil with about 4% to about 30% of an inorganic complexing agent, said complexing agent being insoluble in the oil and forming a viscosity increasing complex with the oil is selected from the group consisting of magnesium trisilicate, calcium carbonate, calcium silicate, a codried gel of aluminum hydroxide and magnesium carbonate, magnesium carbonate, ground limestone, ground oyster shells and mixtures thereof,
    admixing about 3% to about 30% of water with the complexed oil to form a uniform dispersion,
    admixing a sweetening agent, and a sensory masking agent in an amount sufficient to sensory mask the unpleasant edible oil resulting in a pleasant edible oil with the complexed oil and water mixture, and charging the resulting composition to an aerosol container and charging the container with a food grade propellant in an amount, of about 5% to about 50%, sufficient by itself to function as a whipping agent and propellant.

16. The process of claim 15 wherein the unpleasant edible oil is selected from the group consisting of vegetable oil, marine oil, mineral oil and mixtures thereof.

17. The process of claim 15 wherein the vegetable oil is selected from the group consisting of castor oil, linseed oil and mixtures thereof.

18. The process of claim 15 wherein the oil is a marine oil is selected from the group consisting of fish liver oil, fish oil, whale oil, seal oil, marine oil concentrates, marine oils containing at least one omega-3 fatty acid and mixtures thereof.

19. The process of claim 15 wherein the oil is fish oil.

20. The process of claim 15 wherein the oil is marine oil and the marine oil comprises from about 10% to about 60% of at least one omega-3 fatty acid by weight of the fish oil.

21. The process of claim 15 wherein the sweetening agent is present in an amount from about 0.02% to about 10% by weight of the total composition.

22. The process of claim 15 wherein the complexing agent is selected from the group consisting of magnesium trisilicate, calcium carbonate, calcium silicate, a codried gel of aluminum hydroxide and magnesium carbonate, magnesium carbonate, ground limestone, ground oyster shells and mixtures thereof.

23. The process of claim 13 wherein the complexing agent is magnesium trisilicate.

24. The process of claim 13 wherein the sweetener is selected from the group consisting of amino acid based sweeteners, dipeptide sweeteners, aspartame, glycyrrhizin, saccharin and its salts, acesulfame and its salts, cyclamate and its salts, steviosides, talin, dihydrochalcone compounds, sucralose and mixtures thereof.

25. The process of claim 13 wherein the sensory masking agent is selected from the group consisting of a taste masking agent, an odor masking agent and mixtures thereof.

26. The process of claim 15 wherein the taste masking agent is selected from the group consisting of: anethole, dihydroanethole, eugenol, vanillin, ethyl vanillin, ethyl maltol and mixtures thereof, and the odor masking agent is selected from the group consisting of natural and artificial; lime, lemon, orange, pineapple, grapefruit, cinnamon, clove, bay, allspice, anise, wintergreen, spearmint, peppermint, benzaldehyde, cherry and mixtures thereof.

27. The composition of claim 1 wherein the oil is caster oil.

28. The composition of claim 1 wherein the oil is cod liver oil.

* * * * *

UNITED STATES PATENT AND TRADEMARK OFFICE
CERTIFICATE OF CORRECTION

PATENT NO. : 4,780,309

DATED : October 25, 1988

INVENTOR(S) : Navin M. Geria; Shirley A. Barcelon; Alfred Oppenheimer; Mamoun M. Hussein It is certified that error appears in the above-identified patent and that said Letters Patent is hereby corrected as shown below:

In Claim 5, line 2, insert --which-- after "oil."

In Claim 14, line 2, change "0.0%" to --0.01%--.

In Claim 23, line 1, change "13" to --15--.

In Claim 24, line 1, change "13" to --15--.

In Claim 25, line 1, change "13" to --15--.

Signed and Sealed this

Ninth Day of May, 1989

Attest:

Attesting Officer

DONALD J. QUIGG

Commissioner of Patents and Trademarks